(12) United States Patent
Kretschmann et al.

(10) Patent No.: US 8,366,297 B2
(45) Date of Patent: Feb. 5, 2013

(54) OPERATING LIGHT WITH LED ORIENTATION BY MEANS OF POSITIVE LOCKING

(75) Inventors: Hanno Kretschmann, Hamburg (DE); Sven Müller, Honigsee (DE); Carsten Timm, Seth (DE); Christian Elsenbach, Bargteheide (DE)

(73) Assignee: Dräger Medical GmbH, Lübeck (DE)

( * ) Notice: Subject to any disclaimer, the term of this patent is extended or adjusted under 35 U.S.C. 154(b) by 0 days.

(21) Appl. No.: 13/169,213

(22) Filed: Jun. 27, 2011

(65) Prior Publication Data
US 2012/0182731 A1 Jul. 19, 2012

(30) Foreign Application Priority Data
Jan. 13, 2011 (DE) .......................... 10 2011 008 474

(51) Int. Cl.
*F21V 33/00* (2006.01)
(52) U.S. Cl. .......... 362/249.04; 362/249.02; 362/311.02
(58) Field of Classification Search ............. 362/249.02, 362/249.03, 249.04, 311.02
See application file for complete search history.

(56) References Cited

U.S. PATENT DOCUMENTS

| | | | |
|---|---|---|---|
| 6,299,337 B1 * | 10/2001 | Bachl et al. ................... | 362/545 |
| 7,690,813 B2 * | 4/2010 | Kanamori et al. ....... | 362/249.02 |
| 2008/0238323 A1 | 10/2008 | Chan et al. | |
| 2010/0277666 A1 * | 11/2010 | Bertram et al. ................. | 349/61 |

FOREIGN PATENT DOCUMENTS

| | | |
|---|---|---|
| DE | 100 34 594 A1 | 1/2002 |
| EP | 2 031 295 A1 | 3/2009 |

\* cited by examiner

*Primary Examiner* — Laura Tso
(74) *Attorney, Agent, or Firm* — McGlew and Tuttle, P.C.

(57) ABSTRACT

An operating light is provided with a basic body (1) with flat contact surfaces (2), which are oriented with mutually different angular orientations of the respective surface normals to the working point of the operating light. A printed circuit board (6), having an underside which is flat in a premounted position, has rigid sections (8) with flat upper side surfaces pointing towards a working point of the operating light and sections (7) flexible in a preferred direction, which extend between the rigid sections (8). Light-emitting diodes (9) are arranged on the rigid sections of the printed circuit board. A lens holder (22) is provided with optical lenses (13) for the light-emitting diodes (9). The rigid sections of the printed circuit board can be placed on the contact surfaces (2) of the basic body (1) in a positive-locking manner in a mounted position, so that the light-emitting diodes (9) have lighting directions corresponding to the angular orientations of the contact surface normals. The lens holder (22) can be fixed to the basic body (1) such that a mechanical force can be indirectly or directly transmitted by the lens holder onto the printed circuit board (6), so that at least the rigid sections (8) thereof are pressed from the premounted position into the mounted position in a positive-locking manner against the contact surfaces (2) of the basic body (1).

20 Claims, 8 Drawing Sheets

OPERATING LIGHT WITH LED ORIENTATION BY MEANS OF POSITIVE LOCKING

CROSS REFERENCE TO RELATED APPLICATIONS

This application claims the benefit of priority under 35 U.S.C. §119 of German Patent Application DE 10 2011 008 474.6 filed Jan. 13, 2011, the entire contents of which are incorporated herein by reference.

FIELD OF THE INVENTION

The present invention pertains to an operating light, with a basic body, with at least one printed circuit board flexible in predetermined sections, with light-emitting diodes provided in the other sections, as well as with at least one lens holder with optical lenses for the light-emitting diodes. Contact surfaces of various angular orientations, on which the nonflexible areas of the printed circuit board with light-emitting diodes lie, are provided on the basic body, so that the light-emitting diodes have individual lighting directions determined by the angular orientations of the contact surfaces.

BACKGROUND OF THE INVENTION

In such an operating light, the contact surfaces provided in the basic body as well as the angular orientation thereof determine the direction in which the light of the light-emitting diodes is emitted. The contact surfaces advantageously have different angles, so that the light of the light-emitting diodes is directed onto a common area, e.g., a working point.

EP 2 031 295 A1 discloses a medical treatment light with light-emitting diodes, in which a plate-like carrier element with a mounting surface curved continuously or in a stepped manner inwardly, along which the light-emitting diodes are arranged, is provided, so that each light-emitting diode is oriented at a different angle.

SUMMARY OF THE INVENTION

The object of the present invention is to perfect a light of the type mentioned in the introduction such that accurate orientation of the light-emitting diodes and lenses is guaranteed along with the simplest possible mounting.

This object is accomplished according to the present invention by the lens holder being shaped and fixed to the basic body such that it exerts mechanical pressure on the printed circuit board, so that the essentially nonflexible areas thereof, on which the light-emitting diodes are provided, are pressed against the contact surfaces of the basic body and are oriented with the shape thereof.

In particular, the object is accomplished in one embodiment by an operating light, having a basic body with flat contact surfaces, which are oriented towards the working point of the operating light, each with different angular orientations of the respective surface normals. A printed circuit board is provided having an underside which is flat in a premounted position, furthermore having rigid sections with flat upper side surfaces pointing towards a working point of the operating light and sections that extend between the rigid sections and are flexible in a preferred direction. Light-emitting diodes are arranged on the rigid sections of the printed circuit board. A lens holder is provided, into which a plurality of optical lenses for the light-emitting diodes are inserted. The rigid sections of the printed circuit board can be placed on the contact surfaces of the basic body in a positive-locking manner in a mounted position, so that the light-emitting diodes have lighting directions corresponding to the angular orientations of the contact surface normals. The lens holder can be fixed to the basic body such that a mechanical force can be indirectly or directly transmitted by the lens holder onto the printed circuit board, so that at least the rigid sections thereof are pressed from the premounted position into the mounted position in a non-positive manner against the contact surfaces of the basic body.

This design has two advantages along with simple mounting. On the one hand, due to the force that is exerted by the lens holder on the printed circuit board, the essentially nonflexible areas of the lens holder are pressed by bending the flexible areas onto the contact surfaces provided in the basic body, so that these nonflexible areas lie flatly in contact with and on the contact surfaces. This in turn has the consequence that the light-emitting diodes provided in the nonflexible areas on the printed circuit board are oriented corresponding to the angular orientation of the contact surfaces. Each of the light-emitting diodes can thus be oriented as desired—only the angular orientations of the contact surfaces are to be selected correspondingly when constructing the basic body.

On the other hand, as a consequence of these orientations of the light-emitting diodes and of the nonflexible areas of the printed circuit board, the lenses inserted into the lens holder are also oriented correctly corresponding to the particular light-emitting diode associated with them, because the lens is seated on the part of the printed circuit board surrounding the light-emitting diode and thus assumes the orientation thereof in relation to the working point.

These orientations require no separate adjustments, because the orientations are inevitably correct as a consequence of the pressure that is exerted by the lens holder due to bending of the flexible areas of the printed circuit board. The orientations are arranged, in general, such that the light-emitting diodes are oriented towards a working point or work area.

Provisions are made according to one embodiment of the present invention for the lens holder to exert mechanical pressure on the printed circuit board—or on the light-emitting diodes provided therein—via the lenses inserted into it. In this way, no special contact areas are needed on the lens holder, and the lenses themselves are likewise oriented as well, because the pressure is exerted via them.

According to another embodiment of the present invention, the lenses have flat lower surfaces, which exert pressure on flat surfaces of the printed circuit board. Thus, both the parts of the printed circuit board and the lenses are inevitably adjusted corresponding to the contact surfaces and the orientation thereof.

To transmit the pressure between the lens holder and lenses, the lenses have an edge according to another embodiment of the present invention. Thus, there is no light shadowing.

The lens holder is to be fixed to the basic body in a compression-proof or tension-proof manner. For this, according to another embodiment of the present invention, the lens holder is fixed to the basic body by means of screw connection, bonding, clamping or by means of a spring clip connection. A spring clip connection utilizes the force of a spring to fix the different components by self-locking by the sharp edges of the spring digging into the clamping sites under load. By fixing the lens holder to the basic body, the printed circuit board with LEDs located thereon as well as all corresponding lenses are automatically fixed and oriented.

To form an easy-to-handle and easy-to-mount unit, the printed circuit board and lens holder form one LED unit according to another embodiment of the present invention, wherein the printed circuit board is fixed to the lens holder, preferably loosely by means of a spring clip connection or a plug type connection.

To achieve the best possible dissipation of the heat generated by the light-emitting diodes, the basic body is made of a heat-conducting material, especially metal or a metal alloy according to another embodiment of the present invention.

It may be advantageous, as is provided according to another embodiment of the present invention, to provide a film between the basic body and printed circuit board for electrical insulation, which is heat-conducting. Thus, electric insulation can be achieved between the basic body and printed circuit board and good heat dissipation can nevertheless be achieved. As an alternative, a heat-conducting paste may be applied to the upper side of the basic body or to the underside of the printed circuit board.

Some exemplary embodiments of the present invention are explained in more detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
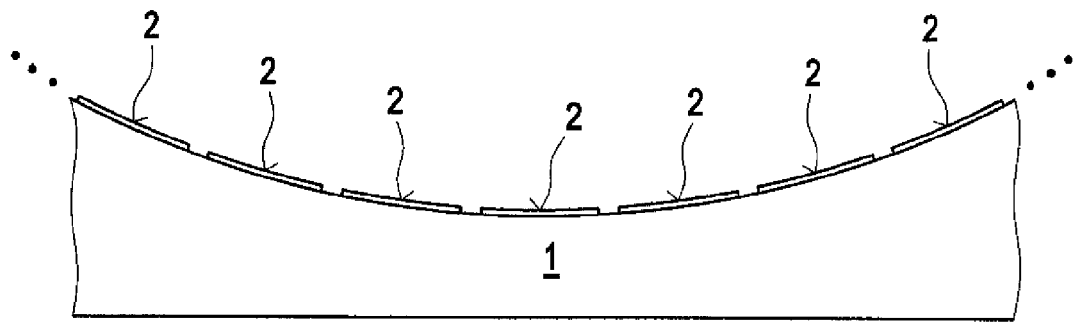
FIG. 1A is a side view of a basic body of an operating light according to the present invention.
Figure 1B:
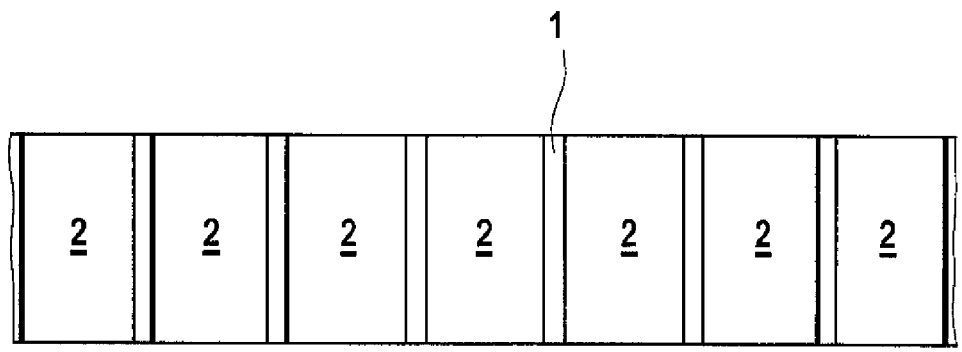
FIG. 1B is a top view of the basic body of an operating light according to the present invention.

Referring to the drawings in particular, FIGS. 1A and 1B show a side view and top view of a detail of a basic body 1 of an operating light according to the present invention with contact surfaces 2. The contact surfaces 2 are arranged in a semicircular pattern next to each other and have different angular orientations.

Figure 2:
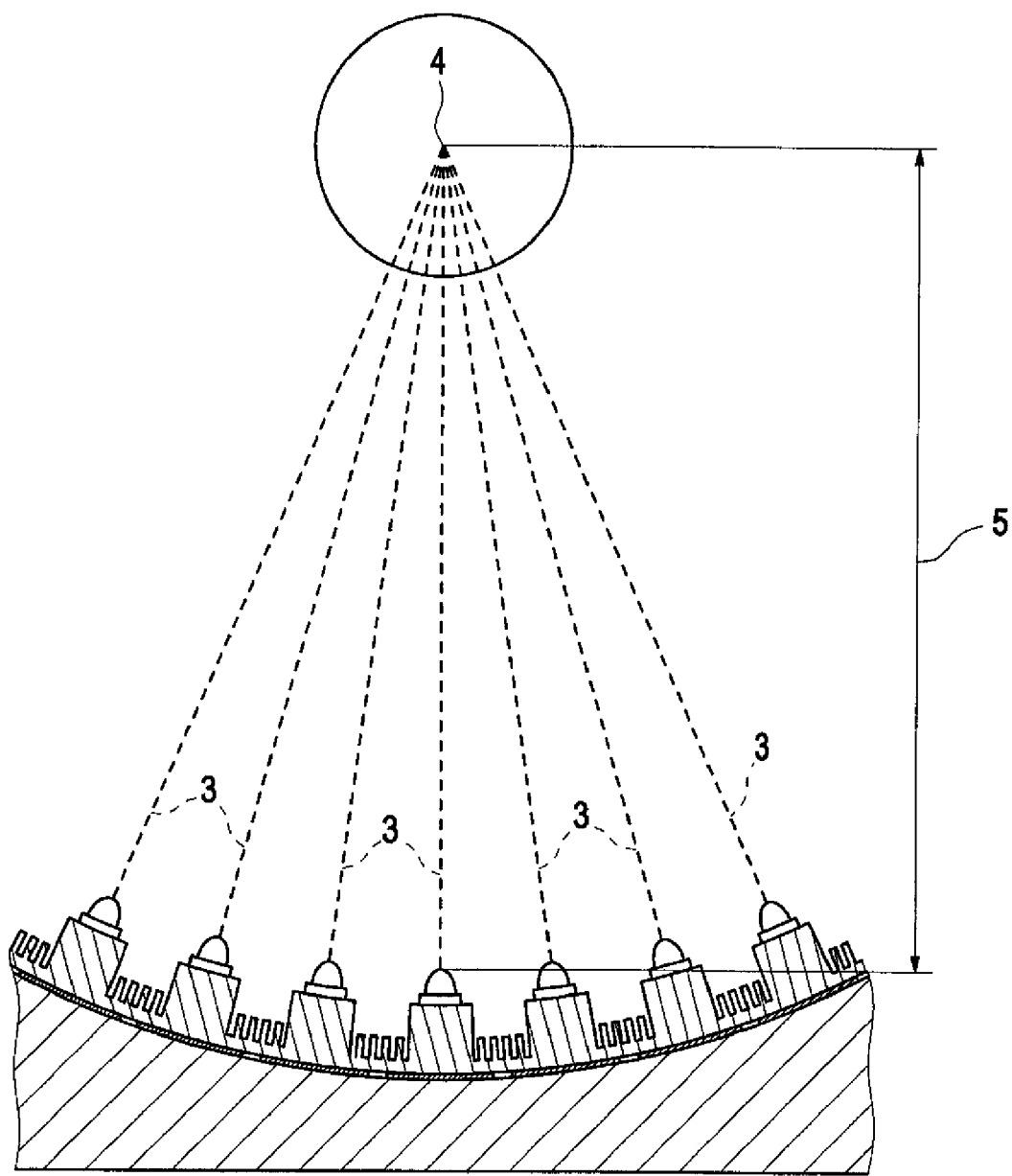
FIG. 2 is a schematic view of the orientation of the contact surfaces of the basic body according to FIG. 1.

These differing angular orientations are such, as is schematically indicated in FIG. 2, that the vertical lines to the bases and later beam axes 3 of the LEDs meet in a point 4 or area to be lit by means of the light at a working distance 5. The contact surfaces 2 are arranged in this exemplary embodiment in the form of a spherical surface cutout, the working point 4 being located in the (imaginary) origin of the sphere.

Figure 3:
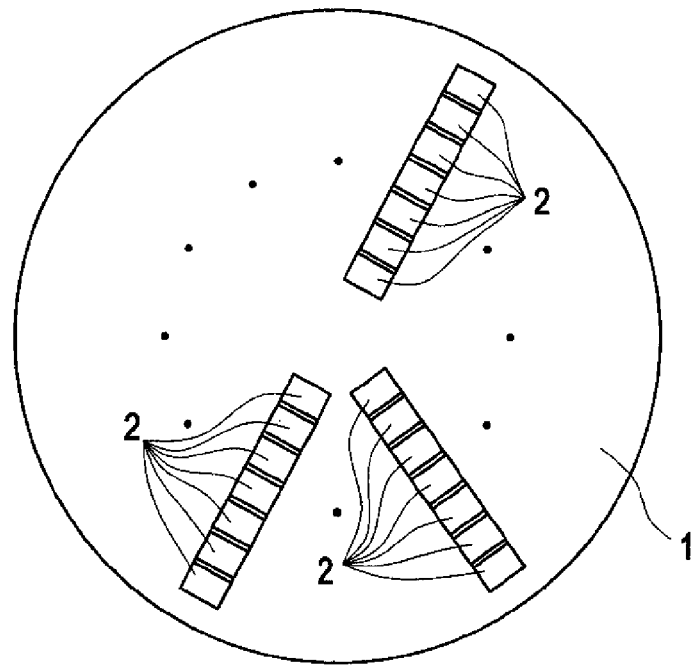
FIG. 3 is a round operating light with a plurality of LED units according to the present invention.

FIG. 3 shows that an operating light according to the present invention with basic body 1 may have contact surfaces 2 arranged radially in a plurality of rows.

Figure 4A:
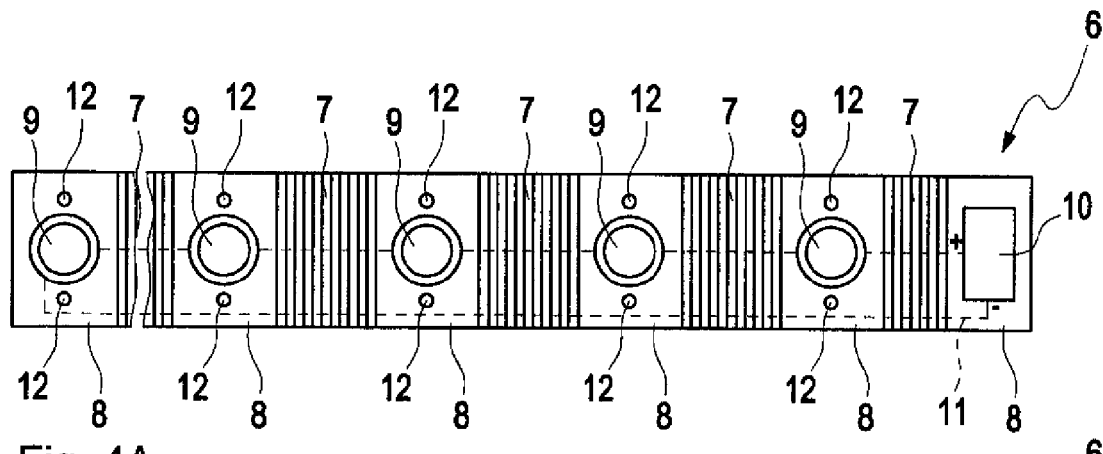
FIG. 4A is a top view of a board with light-emitting diodes for an operating light according to the present invention.
Figure 4:
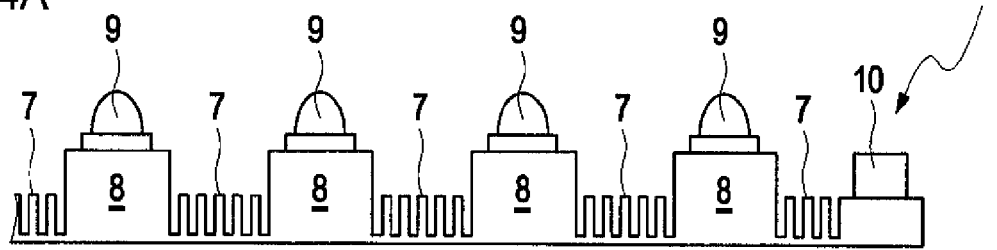
FIG. 4B is a side view of a board with light-emitting diodes for an operating light according to the present invention.

FIGS. 4A and 4B show a side view and a top view of a strip-shaped printed circuit board 6 with light-emitting diodes 9 for an operating light according to the present invention. The printed circuit board 6 has flexible sections 7, which are bendable. The light-emitting diodes 9 are arranged, by contrast, in nonflexible sections 8 of the light-emitting diode 6.

The printed circuit board may be, for example, a Semiflex PCB board, where strip conductors 11 are provided for the electric supply of the light-emitting diodes 9 on the underside of the printed circuit board 6. A part of the material of the printed circuit board may be removed, for example, milled off, in the flexible areas 7 to obtain a flexible construction, but the strip conductors 11 being led on the underside, which preferably consist of copper, remain uncompromised.

An outlet 10 for supplying a supply voltage for the light-emitting diodes 9 may be provided at one end of the printed circuit board 6. The light-emitting diodes 9 are connected in a series connection by means of the strip conductors 11.

Furthermore, holes or openings 12, which are used to position lenses, as will be explained in more detail below, are provided in the printed circuit board 6.

Figure 5:
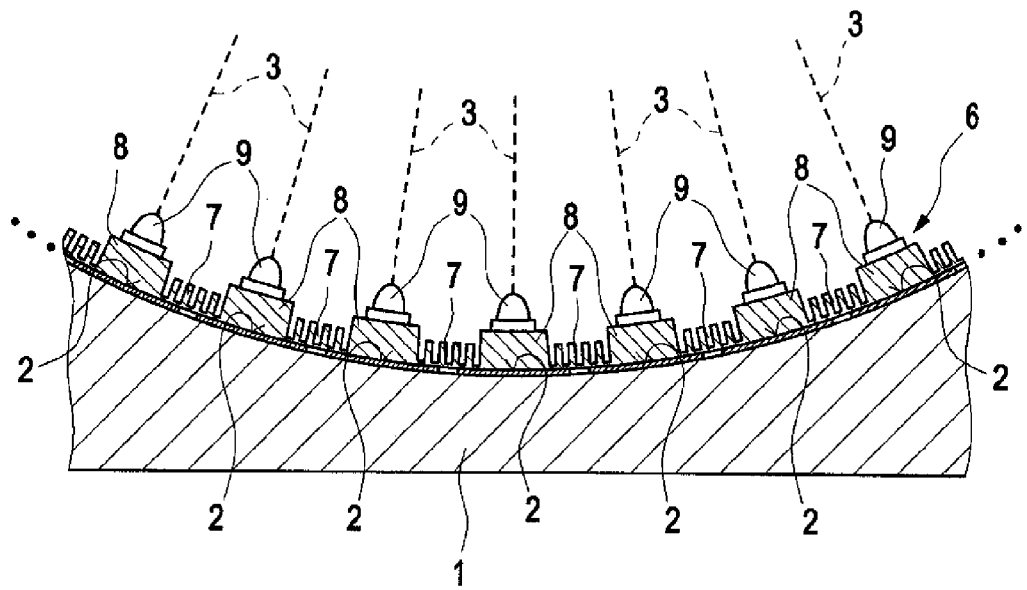
FIG. 5 is a board according to FIG. 4 placed on a basic body according to FIG. 1.

FIG. 5 shows a printed circuit board 6, which is placed on a basic body 1, wherein the nonflexible sections 8 lie on the contact areas 2 and are thus oriented such that the beam axes 3 have the desired direction.

The basic body 1 is also used in this arrangement as a cooling body, onto which the heat produced by the light-emitting diodes can be drawn off.

Figure 6A:
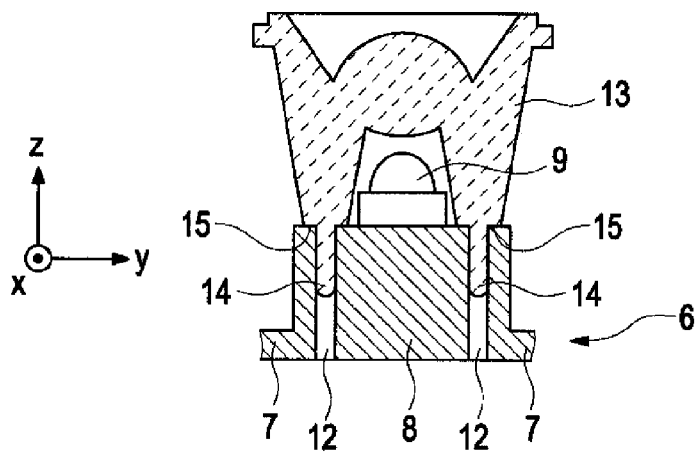
FIG. 6A is a detail sectional view of a board with a light-emitting diode and a lens associated therewith.
Figure 6B:
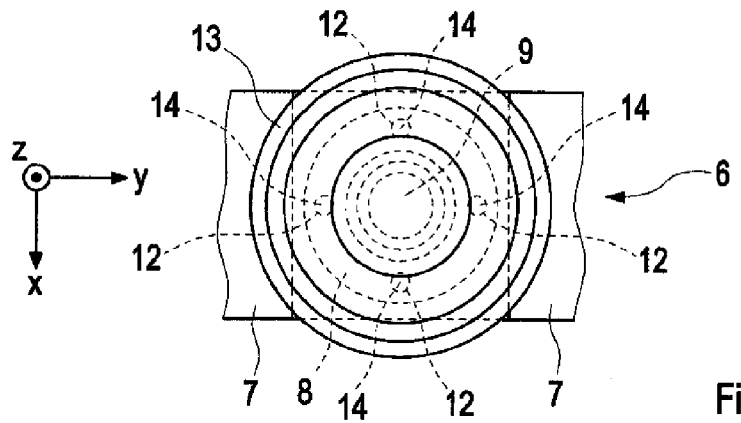
FIG. 6B is a detail of a board in a sectional view and in a top view with a light-emitting diode and a lens associated therewith.

FIGS. 6A and 6B show sectional views of a nonflexible part 8 of a printed circuit board 6 with a light-emitting diode 9. Holes 12 are provided in the area of the light-emitting diode 9 in this nonflexible part 8.

A lens 13 associated with light-emitting diode 9 is provided, whose positioning feet 14 are inserted into holes 12. Lens 13 is thus positioned relative to holes 12 and hence also relative to light-emitting diode 9, so that the lens and LED axes lie one on top of another, with the consequence that both the emission direction is as desired, and tilting of lens 13 is ruled out as well, because lens 13 with its flat lower edge 14 lies on the printed circuit board.

Figure 7:
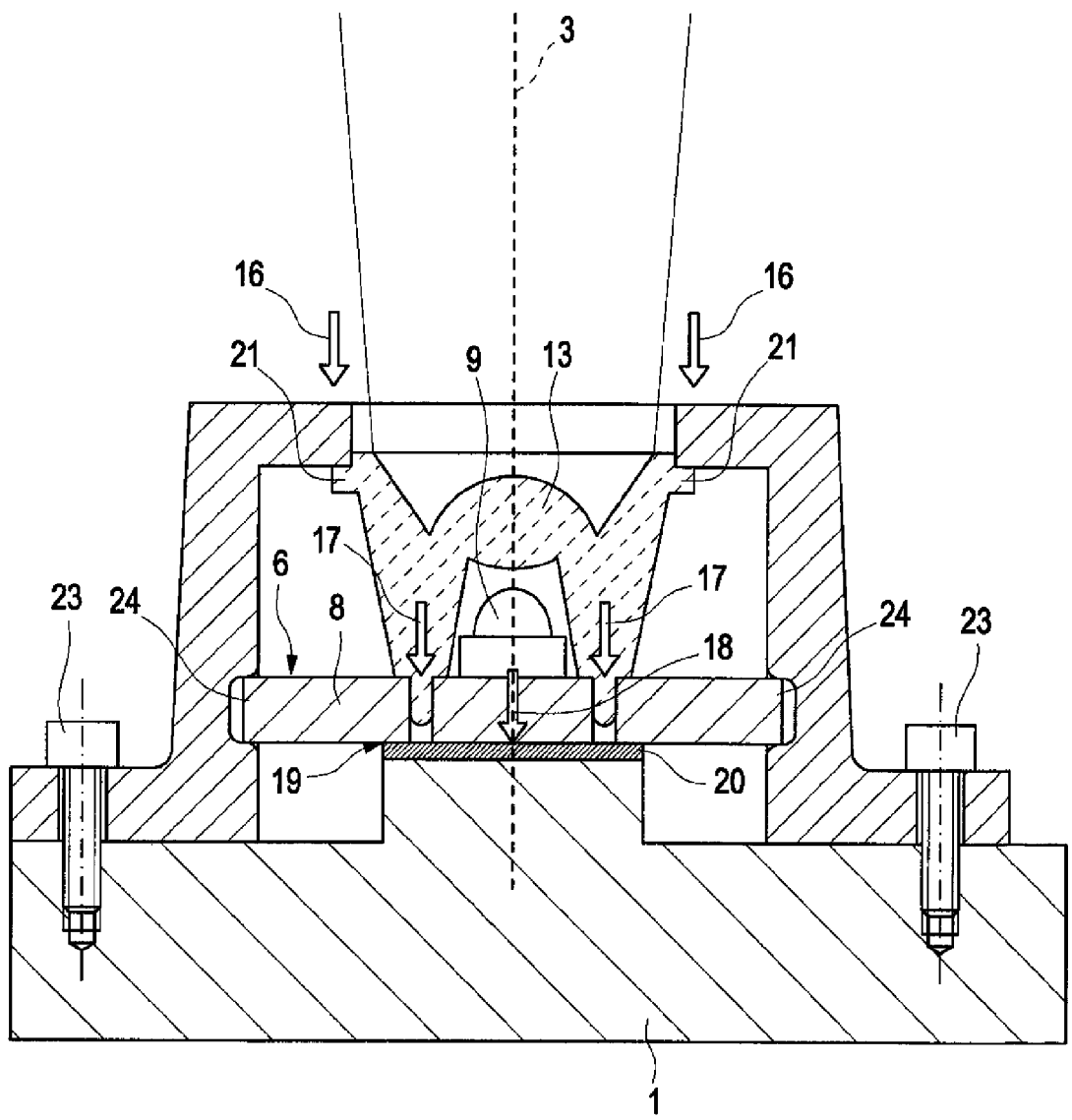
FIG. 7 is a sectional view according to FIG. 6 on an enlarged scale.

FIG. 7 shows a sectional view of a detail of the basic body 1 with a detail of a nonflexible part 8 of the printed circuit board 6 with a light-emitting diode 9 and with a lens 13 associated therewith. Furthermore, a lens holder (22 in FIG. 8) is provided.

Fixation of lens 13 relative to light-emitting diode 9 is brought about by a pressing force (symbolized by arrow 16) at the edge thereof along the axis thereof on the nonflexible part 8 of the printed circuit board. The pressing force of the lens (symbolized by arrow 17) on part 8 of the printed circuit board is transmitted to the basic body 1 (symbolized by arrow 18), as a result of which part 8 of the printed circuit board is pressed at the same time onto basic body 1 in this area in a non-positive manner (symbolized by marking 19) and is thus oriented and fixed according to the shape of the basic body.

A thin heat-insulating film 20, which electrically insulates the strip conductors 11 against the basic body 1, may be located between the printed circuit board 6 and basic body 1. Good heat transfer from part 8 of the printed circuit board, especially through the film 20, into basic body 1 is also achieved by means of the pressing force 18 for drawing off heat from the light-emitting diode 9. At its upper edge, lens 13 has a projecting area 21, which is pressed by the lens holder (22 in FIG. 8). The lens holder is cut out in a circular pattern in this area. Lens 13 is thus pressed by the lens holder in a circular pattern at its upper edge at projecting area 21 downwardly in the direction of part 8 of the printed circuit board.

In order not to have to orient and fix each lens 13 relative to the light-emitting diode associated therewith, the correspondingly shaped lens holder 22 is used for simultaneously fixing a plurality of lenses 13. All lenses 13 are pressed with the lens holder with the circular cutouts thereof on the optical exit surfaces of the lenses at the edges 21 thereof simultaneously and together onto the nonflexible parts 8 of the board. This is brought about by means of screw connections 23 between lens holder and basic body 1. The nonflexible parts 8 of the printed circuit board are pressed onto the basic body and adapt themselves to same in a non-positive manner. As a result, a plurality of light-emitting diode-lens combinations are oriented and fixed in one mounting operation.

In addition, there exists a loose, non-fixing fastening 24 between the printed circuit board 6 and lens holder, for example, by means of a spring clip connection or screw connection. This is used to create a portable modular unit. The flux of forces from the lens holder through lens 13 and through board 8 to basic body 1 is short-circuited here (through the lens holder).

Figure 8:
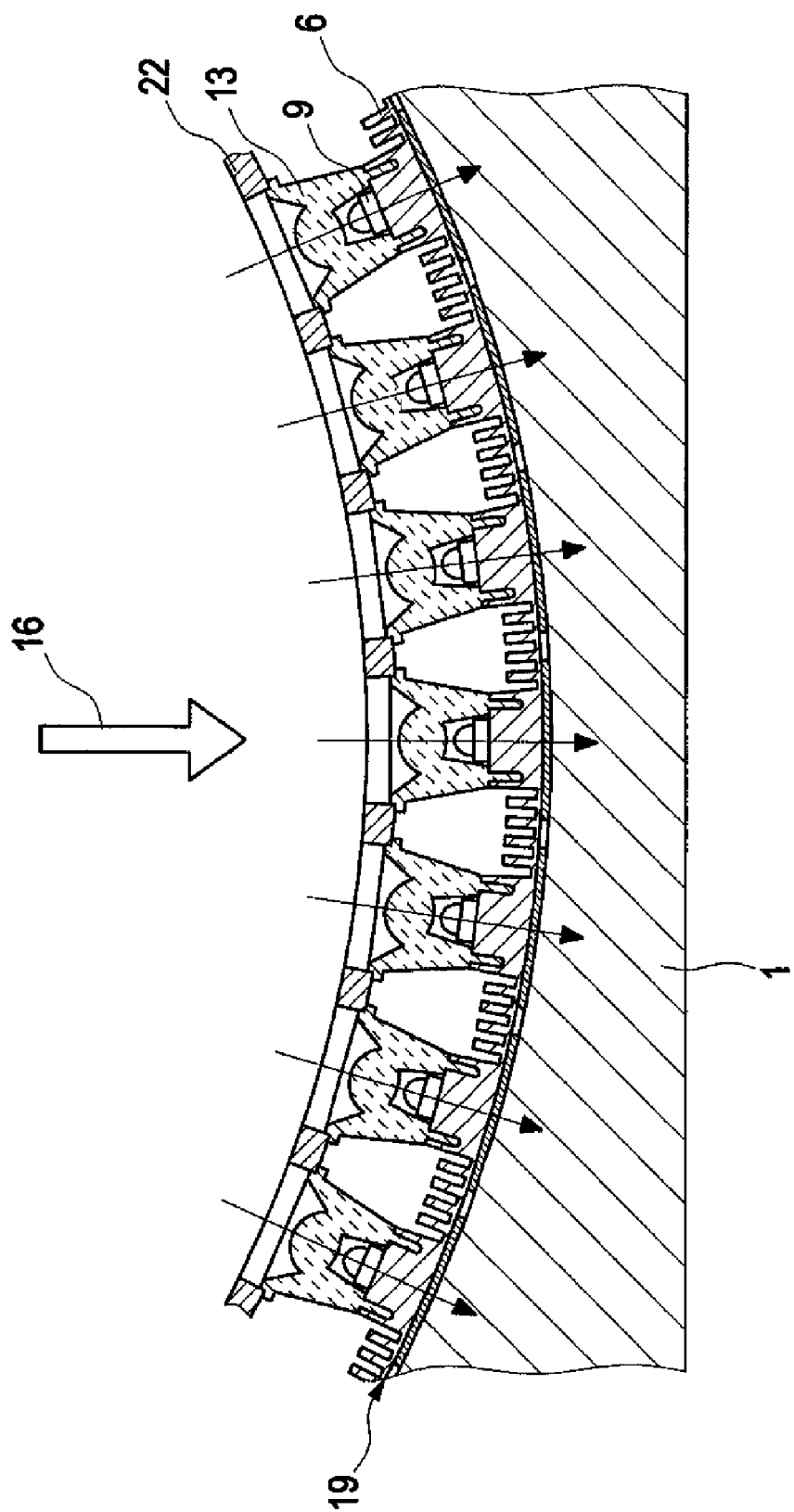
FIG. 8 is a side view of an operating light according to the present invention with a basic body, board, light-emitting diodes, lens holder and lenses.

FIG. 8 shows a view corresponding to FIG. 5 with lenses 13 attached and with lens holder 22. Arrow 16 symbolizes the pressing pressure explained above, which ensures correct orientation of the parts 6 of the printed circuit board and of the light-emitting diodes 9 with lenses 13 thereof.

Figure 9A:
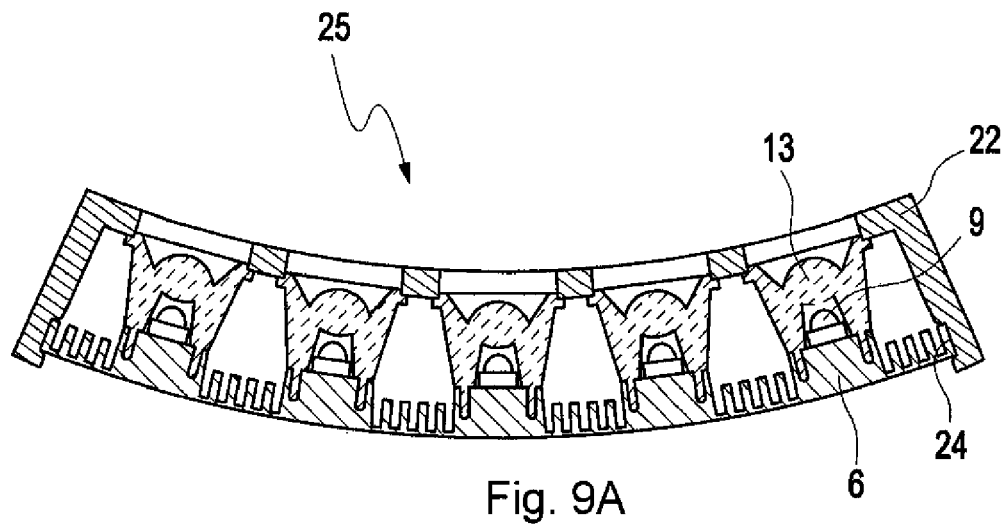
FIG. 9A is a sectional view according to FIG. 8 with representation of the fixation of the lens holder to the basic body.
Figure 9:
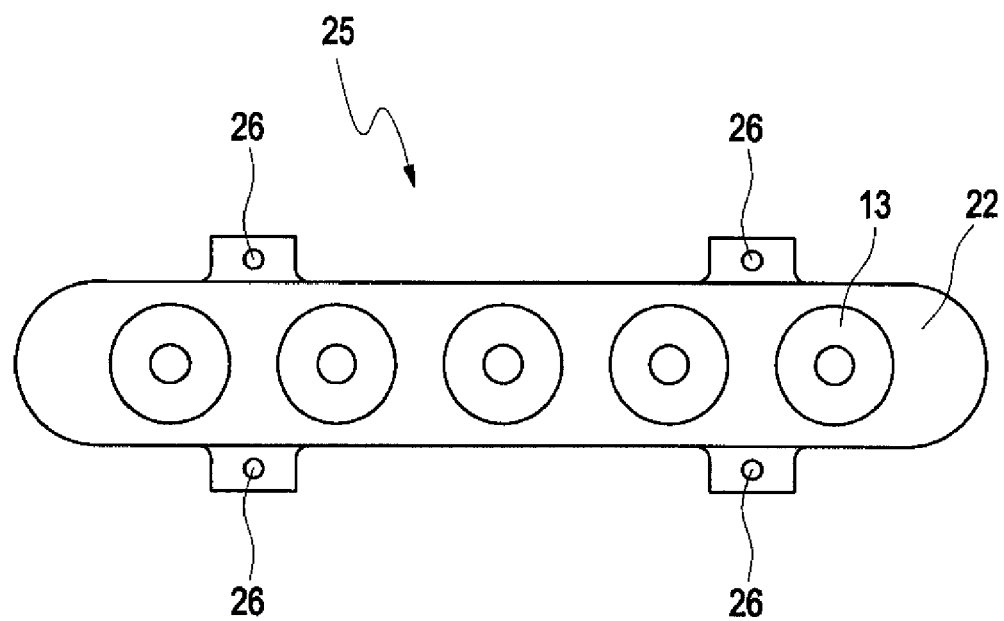
FIG. 9B is a top view according to FIG. 8 with representation of the fixation of the lens holder to the basic body.

FIGS. 9A and 9B show an LED unit 25 comprising a printed circuit board 6, with light-emitting diodes 9, corresponding lenses 13 as well as lens holder 22. As was already explained above, one or more such LED units or lens holders 22 thereof may be advantageously fixed on a basic body 1. In particular, screw holes 26 are provided for this on LED unit 25 or lens holder 22.

Figure 10:
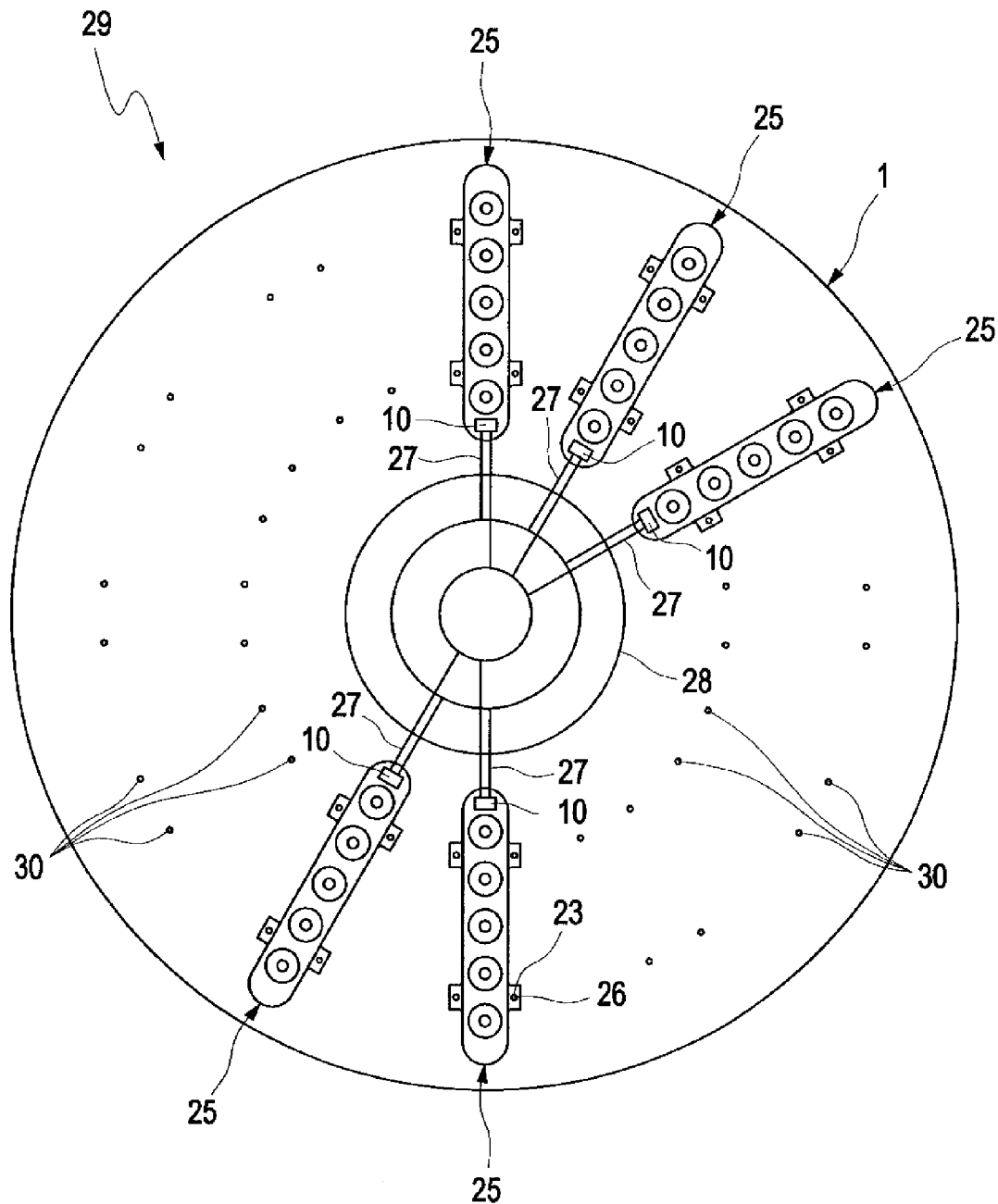
FIG. 10 is a view corresponding to FIG. 3 with cabling.

This becomes clear from FIG. 10, which shows an operating light with a basic body 1, which is designed to receive a plurality of LED units 25, which are arranged axially. The basic body 1 has threaded holes 30. In this way, many light-emitting diodes 9 and lenses 13 can be oriented on a suitably shaped basic body 1, heat-contacted and fixed without individual components having to be mounted individually and without having to employ complicated fixation methods.

FIG. 10 shows, furthermore, that power supply terminals 27 are provided for the outlets 10. The power supply for the modules is brought about centrally via a single distributor board 28. This is possible because the modules receive their power at the end of the module via a plug. An operating light 29 can thus be built up from a small number of LED units 25 and a basic body 1 in a simple manner.

The reference numbers used are used only to enhance understandability and shall not be construed as being limiting by any means, the scope of protection of the present invention being reflected by the claims.

While specific embodiments of the invention have been shown and described in detail to illustrate the application of the principles of the invention, it will be understood that the invention may be embodied otherwise without departing from such principles.

APPENDIX

List of Reference Numbers

1 Basic body
2 Contact surface
3 Beam axis
4 Work area, working point
5 Working distance
6 Printed circuit board
7 Flexible sections of printed circuit board
8 Rigid sections of printed circuit board
9 Light-emitting diode
10 Outlet
11 Strip conductor
12 Hole
13 Lens for light-emitting diode
14 Positioning foot
15 Flat lower edge of lens
16 Force at edge of lens
17 Force from lower edge of lens to printed circuit board
18 Force with which printed circuit board is pressed onto basic body
19 Non-positive/positive-locking adaptation of printed circuit board to basic body
20 Heat-conducting film
21 Projecting area at lens, edge of lens
22 Lens holder
23 Screw connection
24 Fastening of printed circuit board to lens holder
25 LED unit with printed circuit board, light-emitting diodes, lenses and lens holder
26 Screw holes
27 Power supply
28 Distributor board
29 Operating light
30 Threaded hole

What is claimed is:

1. An operating light comprising:
a basic body with flat contact surfaces oriented with different angular orientations each, of respective surface normals, relative to a work area of the operating light;
a printed circuit board having an underside which is flat in a premounted position and having rigid sections with flat upper side surfaces facing the work area of the operating light and sections flexible in a preferred direction, which extend between said rigid sections;
light-emitting diodes, each of said light-emitting diodes being fixed to a respective one of said rigid sections of said printed circuit board and being electrically connected thereto; and
a lens holder with optical lenses for said light-emitting diodes, said rigid sections of said printed circuit board being placed on said contact surfaces of said basic body in a positive-locking manner in a mounted position, so that said light-emitting diodes have lighting orientations corresponding to said contact surface normal, wherein said lens holder is fixed to said basic body such that a mechanical force is indirectly or directly transmitted to said printed circuit board by said lens holder, so that at least said rigid sections of said printed circuit board are pressed from the premounted position into the mounted position against said contact surfaces of said basic body.

2. An operating light in accordance with claim 1, wherein said lens holder exerts mechanical force on said printed circuit board via said lenses provided thereon.

3. An operating light in accordance with claim 2, wherein said lenses each have flat lower surfaces, which exert pressure on flat surfaces of said printed circuit board and are likewise oriented in a positive-locking manner.

4. An operating light in accordance with claim 2, wherein said lenses each have an edge with projecting areas, via which said lens holder exerts pressure on said lenses.

5. An operating light in accordance with claim 1, wherein said lens holder is fixed to said basic body by means of a screw connection, bonded connection, clamped connection, especially spring clip connection.

6. An operating light in accordance with claim 1, wherein said printed circuit board is fixed to said lens holder at least in part by at least one of a spring clip connection and a plug type connection.

7. An operating light in accordance with claim 1, wherein said lenses are oriented in a defined manner in said printed circuit board in a mounted position by means of guide holes and positioning feet provided at said lenses.

8. An operating light in accordance with claim 1, wherein said basic body is made of a heat-conducting material at least in part comprising at least one of a metal and a metal alloy.

9. An operating light in accordance with claim 1, further comprising a film, which is heat-conducting, provided between said basic body and said printed circuit board for electric insulation.

10. An operating light in accordance with claim 1, wherein said printed circuit board and said lens holder form an LED unit, wherein said printed circuit board is fixed to said lens holder at least in part by at least one of a spring clip connection and plug type connection.

11. An operating light in accordance with claim 10, wherein said basic body has a plurality of said contact surfaces, each said LED unit with printed circuit board and lens holder being mounted on one of said contact surfaces.

12. An operating light in accordance with claim 1, wherein said basic body has a shape of a spherical surface segment.

13. An operating light in accordance with claim 11, further comprising:
a power supply for said LED units; and
a distributor board, said power supply and said LED units being connected together centrally via said distributor board.

14. An operating light in accordance with claim 13, wherein said distributor board has plug type connectors connecting outlets of said LED units to said power supply vai said distributor board.

15. An operating light in accordance with claim 14, wherein said plug type connection between said LED units and said distributor board comprises a combination of a one-part spring force-actuated plug on one side and open strip conductor contacts on another side.

16. An operating light comprising:
a basic body with flat contact surfaces, each of said flat contact surfaces having a surface normal angle of orientation relative to a work area of the operating light;
a printed circuit board connected to said basic body, said printed circuit board having rigid sections with upper side surfaces facing the work area of the operating light, each of said rigid sections being associated with one of said flat contact surfaces, said printed circuit board having flexible sections extending between said rigid sections;
light-emitting diodes, each of said light-emitting diodes being fastened to a respective one of said rigid sections of said printed circuit board and being electrically connected thereto;
optical lenses connected to said circuit board, each of said optical lenses being associated with one of said light-emitting diodes; and
a lens holder fixed to said basic body such that a mechanical force is indirectly or directly transmitted to said printed circuit board by said lens holder, so that at least said rigid sections of said printed circuit board are pressed against said contact surfaces of said basic body and have an orientation based on the orientation of the associated one of said flat contact surfaces whereby each of said light-emitting diodes have a lighting orientation corresponding to the surface normal angle of orientation of an associated one of said contact surfaces.

17. An operating light in accordance with claim 16, wherein
said lens holder exerts said mechanical force on said printed circuit board via said lenses provided thereon;
said lenses each have flat lower surfaces, which exert pressure on flat surfaces of said printed circuit board; and
said lenses are likewise oriented in a positive-locking manner, with said lenses each having an edge via which said lens holder exerts pressure on said lenses.

18. An operating light in accordance with claim 17, wherein:
said lens holder is fixed to said basic body;
said printed circuit board is fixed to said lens holder; and
said lenses have positioning feet mounted in guide holes for orienting said lenses in a defined manner.

19. An operating light in accordance with claim 18, further comprising a film provided between said basic body and said printed circuit board for electric insulation wherein:
said film is heat conducting; and
said basic body is made of a heat-conducting material comprising at least one of a metal and a metal alloy.

20. An operating light in accordance with claim 18, further comprising:
a power supply; and
a distributor board wherein:
said printed circuit board and said lens holder form an LED unit, wherein said printed circuit board is fixed to said lens holder;
said basic body has a plurality of said contact surfaces, each said LED unit with printed circuit board and lens holder being mounted with each rigid section including an LED of the circuit board of said LED unit on one of said contact surfaces of said basic body; and
said power supply and said LED units are connected together centrally via said distributor board.

* * * * *